(12) United States Patent
Chatterjee

(10) Patent No.: US 10,004,646 B2
(45) Date of Patent: Jun. 26, 2018

(54) METHODS FOR USING POLYMER FOAM ABSORBENT MATERIALS IN WOUND DRESSINGS

(71) Applicant: Dristi, LLC, Cincinnati, OH (US)

(72) Inventor: Ranjit Chatterjee, Cincnnati, OH (US)

(73) Assignee: Dristi, LLC, Cincinnati, OH (US)

( * ) Notice: Subject to any disclaimer, the term of this patent is extended or adjusted under 35 U.S.C. 154(b) by 860 days.

(21) Appl. No.: 14/463,602

(22) Filed: Aug. 19, 2014

(65) Prior Publication Data

US 2015/0100008 A1    Apr. 9, 2015

Related U.S. Application Data

(60) Provisional application No. 61/887,256, filed on Oct. 4, 2013.

(51) Int. Cl.
*A61F 13/00* (2006.01)
*A61F 13/02* (2006.01)

(52) U.S. Cl.
CPC .. *A61F 13/0206* (2013.01); *A61F 2013/0028* (2013.01); *A61F 2013/00157* (2013.01); *A61F 2013/00336* (2013.01)

(58) Field of Classification Search
CPC ...... A61F 2013/0157; A61F 2013/0028; A61F 2013/0036; A61F 2013/00157; A61F 13/0206; A51F 13/0209; A51F 13/00029; A51F 13/00042
USPC .......................................................... 602/46
See application file for complete search history.

(56) References Cited

U.S. PATENT DOCUMENTS

| | | | |
|---|---|---|---|
| 3,903,232 | A | 9/1975 | Wood et al. |
| 4,049,592 | A | 9/1977 | Marans et al. |
| 4,110,276 | A | 8/1978 | DesMarais |
| 4,613,543 | A | 9/1986 | Dabi |
| 4,664,662 | A | 5/1987 | Webster |

(Continued)

OTHER PUBLICATIONS

Borgquist, Ola, et al., "The influence of Low and High Pressure Levels during Negative-Pressure Wound Therapy on Wound Contraction and Fluid Evacuation", Plastic and Reconstructive Surgery Journal of the American Society of Plastic Surgeons, vol. 127, No. 2, pp. 551-559, 2011.

(Continued)

*Primary Examiner* — Kim M Lewis
(74) *Attorney, Agent, or Firm* — PatentBest; Andrew McAleavey

(57) ABSTRACT

Disclosed are methods for using open-celled polymeric foam wound dressings made from high internal phase emulsions (HIPEs). The wound dressings have a high capillary pressure and may reduce or obviate the need for treatments like negative pressure wound treatment (NPWT). Also disclosed are structures for HIPE foam wound dressings. The HIPE foam wound dressings typically include at least two layers of HIPE foam with different, but homogeneous, average cell sizes. The average cell sizes form a cell size gradient, with cell size typically decreasing from the front or face layer of foam toward the back layer of foam. The back layer of foam may be a collapsed layer, while the front layer or layers may be expanded. Compared with HIPE foams for other absorbent applications, the wound dressing foams may be higher in hydratable salts and higher in initial moisture levels.

30 Claims, 2 Drawing Sheets

(56) References Cited

U.S. PATENT DOCUMENTS

Figure 1:
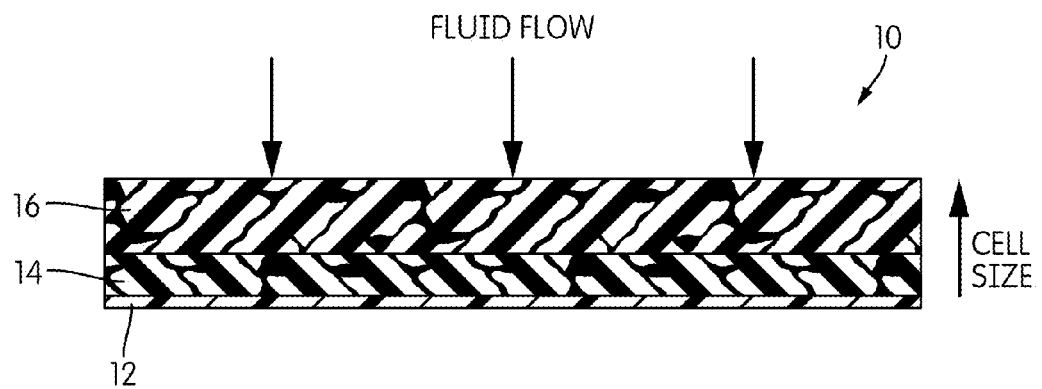

| | | | |
|---|---|---|---|
| 4,752,349 | A | 6/1988 | Gebel |
| 4,969,880 | A | 11/1990 | Zamierowski et al. |
| 5,147,345 | A | 9/1992 | Young et al. |
| 5,260,345 | A | 11/1993 | Desmarais et al. |
| 5,268,224 | A | 12/1993 | Desmarais et al. |
| 5,318,554 | A | 6/1994 | Young et al. |
| 5,331,015 | A | 7/1994 | Desmarais et al. |
| 5,387,207 | A | 2/1995 | Dyer et al. |
| 5,633,291 | A | 5/1997 | Dyer et al. |
| 5,636,643 | A | 6/1997 | Argenta et al. |
| 5,650,222 | A | 7/1997 | Desmarais et al. |
| 5,795,921 | A | 8/1998 | Dyer et al. |
| 6,274,638 | B1 | 8/2001 | Yonemura et al. |
| 2015/0353699 | A1* | 12/2015 | Foudazi ................. C08J 9/0023 521/120 |
| 2017/0267827 | A1* | 9/2017 | Rowan .................... A61F 13/53 |

OTHER PUBLICATIONS

Guillaume, Chaby, et al., "Dressings for Acute and Chronic Wounds A Systematic Review", Arch Dermatol, vol. 143, No. 10, pp. 1297-1304, Oct. 2007.

* cited by examiner

METHODS FOR USING POLYMER FOAM ABSORBENT MATERIALS IN WOUND DRESSINGS

CROSS-REFERENCE TO RELATED APPLICATIONS

This application claims priority to U.S. Provisional Application No. 61/887,256, filed Oct. 4, 2013, the contents of which are incorporated by reference in their entirety.

BACKGROUND OF THE INVENTION

1. Field of the Invention

In general, the invention relates to methods of using polymer foam absorbent materials in wound dressings.

2. Description of Related Art

Since time immemorial, the standard dressing for a wound—the material used to cover a wound, protect it, and absorb blood and other exudates—has been cotton or cotton gauze. Cotton, itself a natural cellulose polymer, is cheap, plentiful, absorbent, and relatively easy to sterilize. Cotton gauze, in pads and rolls, is extremely common in first aid, ambulance, and hospital settings.

Despite its ubiquity, cotton gauze has serious drawbacks. For example, while it is absorbent, it will not draw and sequester fluids and other exudates away from a wound, and it may thus allow bacteria and other harmful elements to remain in contact with the wound and the patient's skin. On a more practical level, once used, cotton gauzes tend to harden and stick to wounds, making them painful to remove and presenting the possibility that removing a used bandage may cause damage or impede healing.

In recent decades, doctors and scientists have come to understand the healing process better. For example, it is now known that moisture is helpful in revascularization and other stages of the healing process, and that it may be helpful if the edges of a wound are kept dry while the interior of the wound is kept moist. However, even though the understanding of the process has improved, chronic wounds, like decubitus ulcers, pressure sores, venous stasis ulcers, infected wounds, deep and open surgical incisions, and burns still present long-term problems and require special care. These chronic types of wounds can require weeks or months to heal, and can easily become infected or cause other complications if not treated adequately. Moreover, there are widely varying opinions on the proper treatment protocols.

While caring for chronic wounds is difficult, and standards of care are still evolving, there is evidence that treatments like negative pressure wound therapy (NPWT) can speed healing. In NPWT, a special, sealed dressing is connected to a pump. The dressing may be, for example, an open-celled foam with an average cell size of greater than about 400 μm that is present to act, essentially, as a filter for the pump—it is typically rigid enough that it will not collapse into the pump, and its cells and structure allow fluid to flow through it under vacuum. When the pump is activated, sub-atmospheric pressures are maintained on a wound. Most commonly, negative pressures between −10 and −125 millimeters of mercury (mm Hg) are used.

While treatment protocols may vary considerably, it has become clear that wound dressings play an important role in wound healing, and scientists and engineers have risen to the challenge of creating more sophisticated materials to use as dressings. For example, moist dressings made with hydrocolloids and hydrogels are known, as are dressings made with polymer foams.

Materials have also been developed for absorptive applications other than wound dressing. For example, the Procter and Gamble company of Cincinnati, Ohio has created an open cell, collapsed polymer foam material, marketed as INFINICEL® in the United States, that is sold primarily for use in menstrual pads. This material, made by polymerizing a high internal phase emulsion (HIPE), is highly absorbent, lightweight, and flexible. In particular, U.S. Pat. No. 5,795,921 to Dyer et al., which is incorporated by reference herein in its entirety, discloses formulations and methods for making this kind of polymer foam such that it has pore sizes appropriate for capturing blood and menses.

The Dyer patent does mention briefly that these types of materials can be used in wound dressings, but does not offer any specific guidance on how they might be used.

SUMMARY OF THE INVENTION

One aspect of the invention relates to a method for dressing a wound. The method comprises dressing the wound with a wound dressing that includes at least contiguous layers of foam. The first layer serves as a face or wound-facing layer of foam, and the second layer serves as a back layer. The first and second layers of foam may be formed by polymerization using a high internal phase emulsion (HIPE), and may have generally homogenous mean cell sizes and, generally homogenous hole sizes between adjacent cells, that form a gradient from a larger, generally homogenous mean cell size and a larger, generally homogeneous hole size, in the first, face layer to a smaller, generally homogenous mean cell size and a smaller, generally homogenous hole size in the second layer. At least one of the two layers may be a collapsed layer of foam, and in some cases, the second or back layer will be a collapsed layer of foam, while the first or face layer will be a layer of expanded foam. In some embodiments of the invention, the wound dressing may have several layers of foam, arranged in a gradient such that the first or face layer has the largest cell and hole sizes and the second or back layer has the smallest cell and hole sizes, and there are layers of foam with intermediate cell and hole sizes between the first and second layers. The method may also comprise replacing the wound dressing once it becomes partially or fully saturated.

In methods according to this aspect of the invention, the negative capillary pressure exerted by a wound dressing on a wound may reduce or obviate the need for negative pressure wound treatment (NPWT). However, in some cases, the methods according to embodiments of the invention may be used in conjunction with NPWT.

Another aspect of the invention relates to the structure and composition of wound dressings made with HIPE foam. As was described above, these dressings will typically include at least two generally homogeneous layers of HIPE foam, with different mean cell and hole sizes in each layer of HIPE foam forming a gradient from larger to smaller as fluid moves from the outer face of the dressing toward a backing with a controlled rate of moisture transmission layer. Additionally, wound dressings according to embodiments of the invention may have higher levels of moisture and hydratable salts, and may, in some cases, be prepared without additional steps to wash out the hydratable salts and without extensive drying to reduce moisture.

These and other aspects, features, and advantages of the invention will be set forth in the description that follows.

BRIEF DESCRIPTION OF THE DRAWING FIGURES

Figure 2:
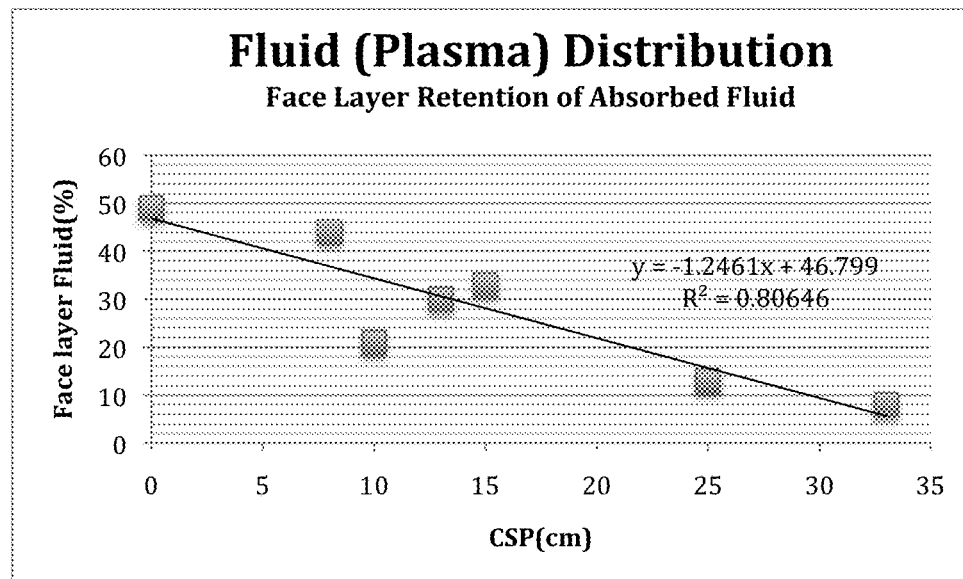
Figure 3:
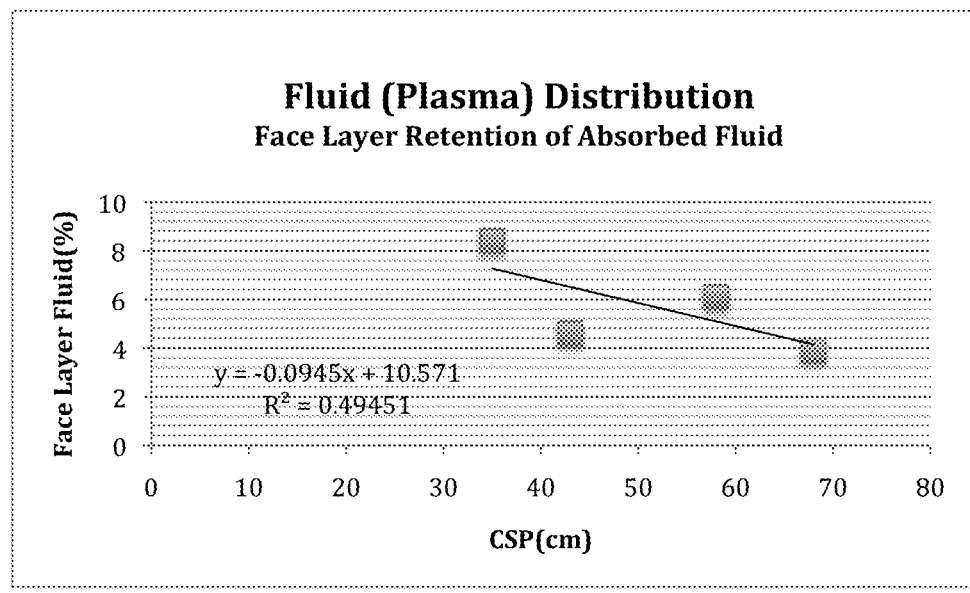

The invention will be described with respect to the following drawing figures, in which:

FIG. 1 is a schematic cross-sectional view of a wound dressing according to one embodiment of the invention; and FIG. 2 is a plot of face layer fluid retention of absorbed fluid for different capillary suction pressures, drawn from the data of Example 2; and FIG. 3 is another plot of face layer retention of absorbed fluid for different capillary suction pressures, drawn from the data of Example 2.

DETAILED DESCRIPTION

The present inventor has found that polymer foam materials made by polymerizing high internal phase emulsions (HIPEs), like the INFINICEL® commercial material marketed by the Procter and Gamble company and the material disclosed in U.S. Pat. No. 5,795,921 to Dyer et al., are particularly suitable for wound care applications. Moreover, the present inventor has also surprisingly found that the capillary pressures exerted by these materials, when they are wetted with fluid, are comparable to at least the lower end of the range of pressures that are commonly used in negative pressure wound treatment (NPWT). Thus, in at least some applications, when an HIPE foam is used in a wound dressing, it may be possible to achieve the effects of NPWT without the difficulty and expense of using a vacuum pump to achieve negative pressure.

Generally speaking, wound dressings according to embodiments of the invention will include at least one layer of an HIPE foam. Optionally, a fluid impervious backing sheet, or a backing sheet with a defined and controlled rate of moisture transmission may be included, as will be described below in more detail. The HIPE foam may be made using the methods disclosed in Dyer et al., cited above, DesMarais et al., U.S. Pat. No. 5,331,015, which is incorporated by reference in its entirety, and other patents that will be set forth below, although some adaptations may be made for wound care applications.

For example, Dyer et al. discloses that hydratable salts, such as calcium chloride, are added to water during the process of forming an HIPE emulsion. The resulting foam is then washed later in the manufacturing process to reduce the level of these salts. In applications in which the object is to create a menstrual pad, this is helpful because menses are typically somewhat viscous, and the presence of salts can increase their viscosity. However, the nature of wound exudates is different; most types of exudates are actually thin and watery. Thus, in wound care applications, it may be possible to omit some of the additional washing steps and allow any ionic salts to remain in the final foam in their existing concentrations.

Additionally, Dyer et al. and other references describe maintaining a low moisture level in the final foam product, typically 2-10%. This facilitates the greatest level of absorption and may be beneficial in other ways, including lower shipping weight and longer shelf life. However, as will be described below in more detail, especially in embodiments where the dressing is intended to reduce or obviate the need for NPWT, a higher initial moisture content may be helpful in achieving and maintaining the material's maximum capillary pressure. Therefore, moisture levels of up to about 20% in the finished HIPE foams may be useful in those embodiments.

While one layer of HIPE foam may be sufficient in a wound dressing for some applications, in many embodiments, it may be particularly advantageous if the wound dressing uses a number of different layers of open cell HIPE foam, each with a different, but generally homogenous, cell size. Commercial HIPE foam products that contain multiple layers of HIPE foam, each layer with different properties, are known in the art, and the Nippon Shokubai Company of Osaka, Japan, among others, has created techniques that can be used to layer HIPE foams and cure them together, reflected, for example, in U.S. Pat. No. 6,274,638 to Yonemura et al., the contents of which are incorporated by reference in their entirety. Of course, the exact method by which multiple layers of HIPE foam are joined into a cohesive whole is not critical, so long as the resulting multilayer construct is continuous and the method of joining does not substantially interfere with capillary action and flow of fluids.

In some embodiments, multiple layers of HIPE foam may be assembled in a gradient, typically with foam layers having larger cell sizes toward the front or face of the dressing and foam layers having smaller cell sizes toward the rear of the dressing. Some of the foam layers may be expanded, while other foam layers may be collapsed. While the inventor does not wish to be bound by any particular theory, the larger cells of the face layer or layers of HIPE foam may trap erythrocytes (i.e., red blood cells) and other larger components of wound exudates, while the smaller cells of the back layers of HIPE foam continue to exert capillary pressure and to draw fluidic and smaller components of the exudate, potentially including bacteria, proteins, and other detrimental elements, away from the wound.

One method of selecting appropriate layers of HIPE foam for a dressing with a multilayer gradient is to measure the capillary suction pressure (CSP) of the HIPE foam using deionized water as the test fluid and to arrange the HIPE foam layers in a dressing such that the CSP increases from the front toward the back of the dressing.

As one example, a wound dressing according to one embodiment of the invention may have a free absorbent capacity of about 10-100 grams of exudate per gram of material (g/g); a face layer of open-celled HIPE foam having cells with an average size of about 20-180 μm and holes between adjacent cells of about 10-30 μm; a back layer of open-celled HIPE foam having cells with an average size of less than about 50 μm, typically about 3-35 μm, and a hole size between adjacent cells of about 2-30 μm; and intervening layers, if present, with foam having cells with an average size in the range of about 40-80 μm, and a hole size between adjacent cells of about 2-30 μm. In this exemplary embodiment, the back layer may be a collapsed foam with a glass transition temperature ($T_g$) of about 35° C. or less. In some embodiments, the HIPE foam of the back layer may have residual hydratable salts in the range of about 1-20% by weight, although, as was described above, the amount or concentration of residual hydratable salts may not be of great concern in all embodiments.

FIG. 1 is a schematic cross-sectional view of an exemplary wound dressing, generally indicated at 10, according to one embodiment of the invention. The wound dressing 10 of the illustrated embodiment includes a film 12 with a controlled rate of vapor transmission, a back layer 14 of an open cell HIPE foam with an average cell size and an average hole size between cells, and a wound-facing front or face layer 16 of an open cell HIPE foam with a different average cell size and a different average hole size. The back layer 14 is a collapsed open cell HIPE foam with an average cell size of 2-20 μm and a thickness of about 0.5 mm collapsed and about 3.0 mm expanded. The second foam layer 16 is an expanded open cell foam with a mean cell size of about 20-150 μm and a thickness of 1-3 mm. If present, the film 12 with its defined moisture transmission rate may extend around the sides of the dressing as well.

However, the film 12 may be an optional component in at least some embodiments. The presence of such a film may prevent bacteria and other wound pathogens from transferring to and infecting caregivers and surfaces around the patient. While that is an advantageous, and sometimes vital, function, a film 12 that is substantially impervious may also prevent the evaporation of aqueous wound exudates, and thus, shorten the life of the wound dressing and potentially affect the rate of healing.

For that reason, the film 12 may have any of a wide range of moisture vapor transmission rates (MVTRs), ranging from 0 grams per square meter per day to about 3,000 grams per square meter per day, with a typical film 12 having an MVTR in the range of 800-1200 grams per square meter per day. While the accepted method for MVTR measurement for impervious backing materials using pure water is convenient and helpful for guidance, a better predictor of dressing performance in duration of use and moisture loss is to test dressing with whole blood or blood plasma in a continuous dosing protocol where real use conditions are simulated. The lack of a film 12, or the presence of a film 12 with a higher MVTR, could allow the back layer 14 of HIPE foam in a wound dressing 10 to re-collapse as fluid evaporates from it, potentially restoring a higher capillary pressure and prolonging the life of the wound dressing 10.

In some embodiments, a cover, typically of a non-woven hydrophilic material, may be provided for the front face of the dressing 10 that faces the wound. However, in wound care applications, particularly when capillary pressure from the dressing 10 is to replace or supplement NPWT, it may be more advantageous to use no cover or intervening layer between the HIPE foams and the wound, such that the maximum amount of fluid can be readily drawn into the HIPE foams. As was described briefly above, higher initial moisture content in the wound dressings 10 may facilitate higher sustained capillary pressures and better performance of the dressings 10.

General guidelines for making suitable HIPE foams for absorbent applications are given in the Dyer et al. patent and in a number of other patents, including U.S. Pat. Nos. 5,331,015; 5,387,207; and 5,650,222, all of which are incorporated by reference in their entireties. While these patents disclose any number of monomers and crosslinkers, preferred monomers are acrylates and styrenes. Calcium chloride and sodium chloride may be preferred salts for hydrophilization. Preferred emulsifiers include diglycerol monoesters. For a high ratio HIPE foam, a second emulsifier may also be used.

With respect to the wound dressing 10 of FIG. 1, the volume to weight ratio of the water phase to the oil phase of the HIPE emulsion is typically in the range of about 20:1 to 50:1 for the front or facial layer 16 and about 40:1 to 125:1 for the back layer 14. Any intervening layers may have ratios of, for example, about 30:1 to 80:1.

Many different materials can be used for the film 12, depending on the use to which the dressing 10 is to be put and the desired rate of fluid evaporation out of the dressing 10. Suitable materials include, but are not limited to, ARGOMEDPLUS® 18411 polyurethane film (3000 MVTR) and TX 1540 polyurethane film (900 MVTR) from Argotec, LLC (Greenfield, Mass.), MICROPORE™ surgical tape (3M, Inc., St. Paul, Minn.) (>3000 MVTR), and polyethylene film of 1 mil thickness (<10 MVTR) (Brentwood Plastics, Inc., St. Louis, Mo.). In some embodiments, the film 12 may be transparent or at least translucent and lightly pigmented, such that it can serve as a visual indicator of when a dressing might require changing. In that case, a light yellow or pink color, indicating that wound exudate had saturated the dressing, might indicate the need for a dressing change.

Wound dressings 10 according to embodiments of the invention may be used in any situation in which a general wound dressing might be used, and they may be made in a variety of shapes and sizes to accommodate wounds of various sizes that are situated in various places on the body. However, they may be particularly helpful with complex, difficult, and chronic wounds, like decubitus ulcers, pressure sores, venous stasis ulcers, infected wounds, deep and open surgical incisions, and burns. They may be used, for example, after surgical wound debridement, to heal skin burns, and to promote skin graft attachment after surgery.

As was described briefly above, wound dressings 10 according to embodiments of the present invention exert maximum capillary pressure when they are wetted and maintain continuous fluid contact with the surface of the wound. For that reason, when a wound dressing 10 is placed on a wound, it may be helpful to secure it in a way that exerts at least sufficient compressive pressure to keep it in contact with the wound. That may involve, for example, securing it with tensioned surgical adhesive tape or wrapping the dressing with roller gauze or self-adhering roller material. Other means of securing dressings are well known to those of skill in the art and may be used in embodiments of the invention. In some embodiments, the dressing 10 itself may include adhesive strips or flaps sufficient to secure the dressing 10.

Of course, in embodiments where a wound dressing 10 is not intended to reduce or obviate the need for NPWT, continuous direct contact with the wound may not be necessary.

Typically, methods for using wound dressings 10 according to embodiments of the invention would involve placing dressings on wounds and replacing those dressings, at intervals, as they became at least partially saturated with wound exudates, or otherwise at regular intervals. For example, the film 12 may be translucent, and the dressing 10 may be replaced when the back layer 14, visible through the backing 12, becomes uniformly discolored. In applications in which the user desires to reduce or obviate the need for NPWT, a dressing 10 may be replaced when the dressing is, for example, up to 50% saturated.

In determining whether a wound dressing 10 can obviate or reduce the need for NPWT, it may be helpful to consider that the standard pressures used in NPWT are predictive of fluid removal via evaporation once the bulk of accumulated wound fluid is removed, whereas the NPWT dressing creates a capillary suction that is effective in removing both accumulated and interstitial fluid as long as there is a fluid continuity between the wound tissue and the dressing at microscopic level. Therefore, wound dressings 10 according to embodiments of the invention may be helpful in a wider range of situations than a direct comparison of NPWT pressure to capillary pressure might indicate.

Although wound dressings 10 according to embodiments of the invention may reduce or obviate the need for NPWT, in some cases, they may be used in conjunction with NPWT, particularly where pressures higher than the capillary pressures exerted by the wound dressings 10 are desired. If wound dressings 10 according to embodiments of the invention are used in conjunction with NPWT, two basic methods may be used. In the first method, NPWT would be administered as usual using a conventional dressing for a period of time, after which the patient would be switched to a wound dressing 10 according to embodiments of the invention. This set of steps might be repeated, so that the patient would receive repeated intervals of conventional NPWT, followed by intervals of coverage with a wound dressing 10.

In a second method of using a wound dressing 10 in conjunction with NPWT, a wound dressing 10 according to an embodiment of the invention would be used as the dressing during NPWT. If the wound dressing 10 is used as an NPWT dressing, it may be perforated to improve air and fluid flow through the dressing. For example, 2-4 perforations per square centimeter, each about 0.5-1.5 mm in diameter, may be formed in the dressing 10.

Generally speaking, whether or not wound dressings 10 according to embodiments of the invention are used alone or as adjuncts to NPWT, they may be used and changed according to schedules or treatment guidelines that assume or expect greater ability to draw fluid away from a wound, prevent maceration around the wound and, in some cases, assume faster healing.

In addition to the methods described above, wound dressings 10 according to embodiments of the invention may be used in methods of monitoring the bacterial load of a wound, or for monitoring for the presence of particular microorganisms. Those methods would typically involve periodically culturing for microorganisms and may alternatively or additionally involve biochemical analysis of inflammatory mediators (e.g., cytokines) in the material of used wound dressings 10 (i.e., by taking a "punch" of the material) at different times or stages of wound treatment.

EXAMPLES

The following examples serve to illustrate aspects of the present invention.

Example 1: Measurement of CSP in HIPE Foams

HIPE foams with cell sizes ranging from about 10-150 μm were selected for testing for use in composite foam dressings. Table 1 below lists the characteristics of the various foams. In Table 1 below, polymer (I) is made according to the teachings of Dyer et al., U.S. Pat. No. 5,795,921; polymer (II) is made according to the teachings of Dyer et al., U.S. Pat. No. 5,633,291; and polymer (III) is made according to the teachings of DesMarais et al., U.S. Pat. No. 5,331,015. All of those patents are incorporated by reference in their entireties.

TABLE 1

| Foam Characteristics. | | | | |
|---|---|---|---|---|
| Foam Type | Oil/water Ratio | Polymer | Cell Size Range (Av. Hole Size) | Hydratable salt |
| A (expanded) | 1:25 | (I) Acrylate | 30-100 μm (15 μm) | calcium chloride |
| B (expanded) | 1:15 | (II) Styrenic | 20-100 μm (13 μm) | calcium chloride |
| C (collapsed) | 1:60 | (III) Styrenic | 4-20 μm (<5 μm) | calcium chloride |
| D (collapsed) | 1:30 | (I) Acrylate | 2-15 μm (<5 μm) | calcium chloride |

The ability of the individual foam sheets to draw fluid via capillary suction (i.e., their capillary suction pressure (CSP)) was measured using an ascending chromatographic technique. A long strip, typically 2.54 cm×60 cm, was allowed to suspend vertically in a tall glass chamber with ample fluid at the bottom and 1 cm of the lower end of the strip dipped in the fluid. The chamber was kept closed to attain stable humidity. For all capillary suction measurements using water, the temperature of water was maintained at 25° C. For measurements with blood plasma as model of wound fluid, the liquid temperature was 37° C. The extent of the strip above the liquid was maintained at ambient temperature, 24-26° C.

Following a 48-hour period of vertical wicking, the strips were removed and cut into 2 cm pieces for weighing. The maximum wicking height with minimal presence of fluid was used for calculation of capillary suction height in mm, and that maximum capillary suction height equates to CSP as measured in millimeters of water. Table 2 below lists measured capillary suction pressures in mm of water. For purposes of comparison, negative pressures in mm of Hg (mercury) were calculated from the measured units. The densities used for conversion from millimeters of water to millimeters of Hg were 1.05 g/ml and 13.53 g/ml for blood plasma and mercury, respectively.

TABLE 2

| Measured CSP of Foams. | | | |
|---|---|---|---|
| Foam | Wicking Fluid | Capillary Suction Pressure (CSP) in mm Water | Calculated Negative Pressure in mm of Hg |
| A | Water | 180 | 13.3 |
|  | Blood Plasma | 200 | 15.5 |
| B | Water | 280 | 20.7 |
| C | Water | 430 | 31.8 |
| D | Water | 510 | 37.7 |
|  | Blood Plasma | 470 | 31.0 |

As shown in Table 2, all open cell foams showed capillary suction capability in the range of 10 to 38 mm Hg, within the range shown to be useful for NPWT. Of the tested foams, the highest negative pressure was achieved with the foam having the smallest cell size, Foam D, with a mean cell size of 8 μm diameter.

These results also demonstrate that the CSP of Foam D with the smallest cell size has a marginally lower CSP for blood plasma or wound fluid due to the lower surface tension of these biological fluids. The other larger cell foams also show differences in CSP for water versus blood plasma, but within experimental error (which is assumed to be about 10%). However, these examples demonstrate that capillary suction pressure measured with water is predictive of foam performance in exerting negative pressure on a wound.

Example 2: Construction of HIPE Foam Composite Dressings

HIPE foam composite dressings with capillary gradients were created by layering the HIPE foams of Example 1. In constructing these composite gradient dressings, the face layer of the dressing (front layer 16, with respect to the illustration of FIG. 1) had the lowest CSP and foams of increasing CSP were chosen for subsequent layers to create the gradient.

All dressings were evaluated in the laboratory for their ability to absorb blood plasma and store it away from the face layer. Dressing pieces measuring 2.54 cm×2.54 cm were exposed to 1.5 to 2.5 mL warm (37° C.) plasma using a peristaltic pump at the rate of 0.5 mL/hr. The wet dressing was allowed to equilibrate in ambient conditions within sealed environment (thus preventing moisture loss) for 24 hours. After 24 hours, each layer was removed to measure fluid content gravimetrically. The fluid content of the face layer was calculated as percentage of total fluid retained in this layer. Results are presented in Table 3. In Table 3 below, delta CSP values were calculated by adding the differences in CSP values of the face layer and any subsequent layers present in the dressing.

TABLE 3

Multilayer Composite Foam Performance

| Dressing | Backing Layer | First Layer Foam | Intermediate Layer(s) Foam | Second Layer Foam | Calculated Delta CSP (cm) | Face Layer Fluid (%) |
|---|---|---|---|---|---|---|
| Two-Layer Dressings ||||||| 
| 1 | None | A | None | A | 0 | 49 |
| 2 | None | C | None | D | 8 | 44 |
| 3 | None | A | None | B | 10 | 21 |
| 4 | None | B | None | D | 13 | 30 |
| 5 | None | B | None | C | 15 | 33 |
| 6 | None | A | None | C | 25 | 13 |
| 7 | None | A | None | D | 33 | 8 |
| Three/Four-Layer Dressings |||||||
| 8 | None | A | B | C | 35 | 8.4 |
| 9 | None | A | C | D | 58 | 6.1 |
| 10 | None | A | B | D | 43 | 4.6 |
| 11 | None | A | B & C | D | 68 | 3.9 |

In Table 3, a lower value of fluid content in the face layer indicated a better performing dressing, in that the dressing created a superior healing environment by drawing moisture away from the skin and leaving minimal wetness of peripheral healthy skin. In FIG. 2, these values are plotted as a function of difference in capillary suction pressures (Delta CSP; water) between the face layer and back layer for two layered composites. Of the tested two-layer composites, the combination of Foam A as the first layer and Foam D as the second layer delivers the highest gradient in suction pressure and minimal (8%) wound fluid next to skin. Of the tested three- and four-layer composites, dressing #11, which used four foams, delivered the highest gradient in suction pressure and the least fluid next to the skin.

The relationship between CSP and face layer fluid retention is shown graphically in the plots of FIGS. 2 and 3. Each of those plots illustrates the data from Example 2 and illustrates a regression line for each set of data.

Example 3: Two-Layer Composite Dressing with Backing Film

It is expected that dressings according to embodiments of the invention will be used for long periods of time without the need to change dressings in order to avoid leaks. The long-term performance of dressings was measured using a continuous infusion protocol in the laboratory. A 6 cm×6 cm absorbent dressing was placed face-down on a glass plate and taped around the sides to avoid any moisture loss from areas other than the back/backing film. The face layer was dosed continuously with warm (37° C.) blood plasma at a rate of 0.5 mL/hour until free fluid was observed at the edges of the dressing. The dressing was removed and weighed to calculate moisture loss using the amount of fluid applied and retained at the end of dosing period. The results are shown below in Table 4.

TABLE 4

Duration of use for dressings
Two-layer composite: First layer foam A/Second layer foam D

| Backing | Moisture Loss (%) in 24 hours | Days to Leak |
|---|---|---|
| None | 89 | >10 |
| MICROPORE ™ (Micro apertures) | 79 | 7 |
| ARGOMEDPLUS ®18411 (MVTR ~3000; E96B, Procedure 1.0 mil, 38° C., 90% RH) | 30 | 2 |
| TX 1540 polyurethane film (MVTR ~900; E-96, Procedure B-upright, 23° C. at 50% RH) | 79 | 7 |
| Polyethylene film (1 mil thickness) | <5 | 1.5 |

While the invention has been described with respect to certain embodiments, the embodiments are intended to be exemplary, rather than limiting. Modifications and changes may be made within the scope of the invention.

What is claimed is:

1. A method for treating a wound, comprising:
    placing a dressing on the wound, the dressing including at least first and second contiguous layers of open: cell foam produced by polymerizing high internal phase emulsions (HIPEs), the first layer of open-cell foam serving as a wound-facing layer and the second layer of open-cell foam serving as a back layer, the first layer of open-cell foam and the second layer of open-cell foam having different average foam cell sizes and different average hole sizes between adjacent foam cells, with an average cell size and an average hole size of the first layer of open-cell foam being greater than an average cell size and an average hole size of the second layer of open-cell foam; and
    replacing the dressing on the wound when the dressing exhibits a characteristic indicating a defined level of at least partial saturation.

2. The method of claim 1, wherein said method is performed without also administering negative pressure wound therapy (NPWT).

3. The method of claim 1, wherein the dressing further comprises a film adjacent to the second layer of open-cell foam, the film having a defined moisture vapor transmission rate (MVTR).

4. The method of claim 3, wherein the defined MVTR of the film is in a range of about 0 to about 3,000 grams per square meter per day.

5. The method of claim 1, wherein the first layer of open-cell foam has an average cell size in a range of about 20 μm to about 180 μm.

6. The method of claim 5, wherein the second layer of open-cell foam has an average cell size of less than about 50 μm.

7. The method of claim 6, wherein the second layer of open-cell foam has a hole size of about 2-30 µm.

8. The method of claim 5, wherein the first layer of open-cell foam has a hole size of about 10-30 µm.

9. The method of claim 5, wherein the dressing further comprises one or more intermediate layers of open-cell HIPE foam interposed between the first layer of open-cell foam and the second layer of open-cell foam, the one or more intermediate layers of open-cell HIPE foam having average cell sizes smaller than or equal to the average cell size of the first layer of open-cell foam and greater than or equal to the average cell size of the second layer of open-cell foam.

10. The method of claim 9, wherein the average cell sizes of the one or more intermediate layers of open-cell HIPE foam are such that a gradient of average foam cell sizes is formed with cell size decreasing from the first layer of open-cell foam toward the second layer of open-cell foam.

11. The method of claim 1, wherein the second layer of open-cell foam is a collapsed layer of foam in at least an initial state.

12. The method of claim 1, further comprising debriding the wound before said placing.

13. The method of claim 1, wherein the wound comprises a burn, a skin graft, a decubitus ulcer, a pressure sore, a venous stasis ulcer, or an infected wound.

14. The method of claim 1, further comprising, after said replacing, culturing a portion of the used dressing to determine a bacterial load or the presence or absence of a particular microorganism, for the wound.

15. A wound dressing, comprising:
a first layer of open-cell foam produced by polymerizing a high internal phase emulsion (HIPE), the first layer of open-cell foam being generally homogeneous in internal structure and having a first average cell size and a first average hole size; and
a second layer of foam adjacent to and in fluid communication with the first layer of foam, the second layer of foam being open-cell foam produced by polymerizing a HIPE and having a second average cell size and a second average hole size less than the first average cell size and the first average hole size, respectively.

16. The wound dressing of claim 15, further comprising a backing sheet adjacent to the second layer of foam, the backing sheet having a preselected moisture vapor transmission rate (MVTR).

17. The wound dressing of claim 16, wherein the preselected MVTR of the backing sheet is in a range of about 0 to about 3,000 grams per square meter per day.

18. The wound dressing of claim 15, wherein the first average cell size is in a range of about 20 µm to about 180 µm.

19. The wound dressing of claim 18, wherein the first average hole size is in a range of about 10-30 µm.

20. The wound dressing of claim 18, wherein the second average cell size is less than about 50 µm.

21. The wound dressing of claim 20, wherein the second average hole size is about 2-30 µm.

22. The wound dressing of claim 15, wherein the dressing further comprises one or more intermediate layers of open-cell HIPE foam interposed between the first layer of open cell foam and the second layer of foam, the one or more intermediate layers of open-cell foam having average cell sizes and average hole sizes greater than or equal to the first average cell size and the first average hole size, respectively, and smaller than or equal to the second average cell size and the second average hole size.

23. The wound dressing of claim 22, wherein the average cell sizes of the one or more intermediate layers of open-cell foam are such that a gradient of average foam cell sizes is formed with cell size decreasing from the first layer of open-cell foam toward the second layer of foam.

24. The wound dressing of claim 15, wherein the second layer of foam is a collapsed layer of foam.

25. The wound dressing of claim 15, further comprising a covering material atop the first layer of open-cell foam.

26. The wound dressing of claim 25, wherein the covering material is nonwoven.

27. The wound dressing of claim 15, wherein the first layer of open-cell foam and the second layer of foam have hydratable salts in the range of about 1-20% by weight.

28. The wound dressing of claim 15, wherein the first layer of open-cell foam and the second layer of foam have moisture levels of 1-20%.

29. The wound dressing of claim 15, wherein the second layer of foam has a glass transition temperature of about 35° C. or less.

30. The wound dressing of claim 29, wherein the second layer of foam is a collapsed layer of foam.

* * * * *